United States Patent [19]

Grollier

[11] Patent Number: 4,820,512

[45] Date of Patent: Apr. 11, 1989

[54] COMPOSITION IN THE FORM OF A GEL FOR INDUCING AND STIMULATING HAIR GROWTH AND FOR DECREASING THEIR LOSS, BASED ON PIPERIDINOPYRIMIDINE DERIVATIVES

[75] Inventor: Jean F. Grollier, Paris, France

[73] Assignee: L'OREAL, Paris, France

[21] Appl. No.: 82,223

[22] Filed: Aug. 6, 1987

[30] Foreign Application Priority Data

Aug. 7, 1986 [LU] Luxembourg .......................... 86548

[51] Int. Cl.$^4$ .............................................. A61K 7/06
[52] U.S. Cl. ....................................... 424/70; 514/63; 514/256; 560/56
[58] Field of Search .................... 424/70; 514/256, 63; 560/56

[56] References Cited

U.S. PATENT DOCUMENTS

| | | | |
|---|---|---|---|
| 3,427,382 | 2/1969 | Haefele | 424/71 |
| 4,139,619 | 2/1979 | Chidsey, III | 424/45 |
| 4,144,332 | 3/1979 | Voorhees | 424/240 |
| 4,517,268 | 5/1985 | Gruber et al. | 430/108 |
| 4,555,466 | 11/1985 | Okada et al. | 430/108 |
| 4,609,603 | 9/1986 | Knapp et al. | 430/108 |

FOREIGN PATENT DOCUMENTS

| | | |
|---|---|---|
| 188793 | 7/1986 | European Pat. Off. |
| WO83/2558 | 8/1983 | PCT Int'l Appl. |
| 2164658 | 3/1986 | United Kingdom |

Primary Examiner—Ellis P. Robinson
Assistant Examiner—P. J. Ryan
Attorney, Agent, or Firm—Fleit, Jacobson, Cohn & Price

[57] ABSTRACT

Composition in the form of a gel for inducing and stimulating hair growth and for reducing hair loss, characterized in that it contains at least one compound of formula (I):

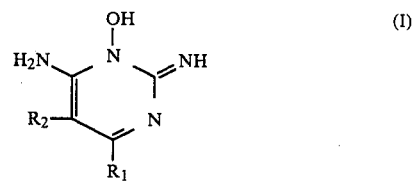

in which $R_1$ denotes a group

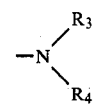

in which $R_3$ and $R_4$ may be chosen from amongst hydrogen, a lower alkyl, preferably containing 1 to 4 carbon atoms, alkenyl, alkylaryl or cycloalkyl group, $R_3$ and $R_4$ may also form a heterocycle with the nitrogen atom to which they are attached, chosen, inter alia, from amongst aziridinyl, azetidinyl, pyrrolidinyl, piperidyl, hexahydroazepinyl, heptamethyleneimine, octamethyleneimine, morpholine and 4-(lower alkyl)piperazinyl groups, it being possible for the heterocyclic groups to be substituted, on the carbon atoms, with one to three lower alkyl, hydroxy or alkoxy groups; the group $R_2$ is chosen from amongst hydrogen, a lower alkyl, alkenyl, alkylalkoxy, cycloalkyl, aryl, alkylaryl, arylalkyl, alkylarylalkyl, alkoxyarylalkyl and haloarylalkyl group, or cosmetically acceptable addition salts with acids, dissolved in an aqueous medium containing at least one $C_1$–$C_4$ lower alcohol and a gelling agent chosen from amongst heterobiopolysaccharides and cellulose derivatives.

14 Claims, No Drawings

COMPOSITION IN THE FORM OF A GEL FOR INDUCING AND STIMULATING HAIR GROWTH AND FOR DECREASING THEIR LOSS, BASED ON PIPERIDINOPYRIMIDINE DERIVATIVES

The invention relates to gels which are effective in inducing and stimulating hair growth and decreasing their loss, based on piperidinopyrimidine derivatives.

Man has a basic number of 100,000 to 150,000 hairs and it is normal to lose 50 to 100 hairs daily. The maintenance of this basic number results essentially from the fact that the life of a hair is subject to a cycle called the pilar cycle during which the hair is formed, it grows and falls before being replaced by a new part which appears in the same follicle.

In the course of a pilar cycle, three successive phases are observed, viz, the anagen phase, the catagen phase and the telogen phase.

During the first phase, referred to as the anagen phase, the hair passes through an active growth period associated with an intense metabolic activity in the bulb region.

The second phase, referred to as the catagen phase, is transitory and it is marked by a slowing down of metabolic activities. During this phase, the hair undergoes an involution, the follicle atrophies and its implantation in the skin appears increasingly shallow.

The final phase, referred to as the telogen phase, corresponds to a rest period for the follicle and the hair finally falls out, pushed by a newly formed anagen hair.

This constant physical renewal process undergoes a natural change during ageing, the hair becomes finer and the cycles thereof become shorter.

Alopecia results when this physical renewal process is accelerated or disturbed, i.e. the growth phases become shorter, the passage of hair into the telogen phase is earlier and hairs fall in larger numbers; successive growth cycles result in increasingly fine and increasingly short hair, which are slowly converted into an unpigmented fluff. This phenomenon may lead to baldness.

The pilar cycle depends on many factors capable of leading to a more or less pronounced alopecia. Among these factors, there may be mentioned nutritional factors, endocrinal factors, nervous factors and the like. The changes in the different categories of hair may be determined with a trichogram.

Compositions which enable the effect of alopecia to be eliminated or reduced and especially hair growth to be induced or stimulated or hair loss to be reduced have been sought in the cosmetic or pharmaceutical industry for many years.

To this end, compounds such as 6-amino-1,2-dihydro-1-hydroxy-2-imino-4-piperidinopyrimidine and the derivatives thereof have already been proposed. Such compounds are described especially in the patent U.S. Pat. No. 4,139,619.

The combination of retinoids with the above-named compounds has also been proposed in the patent WO-A-83/02,558.

Preparations based on 6-amino-1,2-dihydro-1-hydroxy-2-imino-4-piperidinopyrimidine generally contain water, ethyl alcohol and propylene glycol or mixtures of these compounds taken two at a time. However, such compositions have the disadvantage of waxing the hair, increasing their weight, making them oily and sticky. This disadvantage is further enhanced after repeated local applications.

Moreover, these solutions are not very convenient to apply, mainly because of the fact that liquid solutions do not become localized satisfactorily.

The Applicant Company has discovered that it was possible to prepare a composition which is both active in the control of alopecia and which does not have the abovementioned disadvantages of the compositions of the prior art.

The Applicant Company has observed, inter alia, that the use of 6-amino-1,2-dihydro-1-hydroxy-2-imino-4-piperidinopyrimidine in an aqueous gel, which does not irritate the scalp, enabled the efficacy of the active substance to be increased as compared with conventional compositions, using smaller quantities by weight of the active principle than in the forms previously employed and requiring less frequent applications.

The composition according to the invention enables, inter alia, the storage of the active principle in the corneous layer to be promoted, resulting in a prolonged action of the active substance between two applications.

The improved efficacy also appears to be due to the fact that the diffusion of the active substance through the pilosebaceous canal is improved.

Moreover, the composition according to the invention has good cosmetic properties, the hair is not waxed and is not made dull, which also makes it possible to maintain the active substance in contact for a longer period of time, without the need for rinsing.

The subject of the invention therefore consists of a composition in the form of a gel, for inducing and stimulating hair growth and for decreasing their loss, based on piperidinopyrimidine derivatives.

Other subjects of the invention will become apparent on reading the description and the examples which follow.

The composition according to the invention is essentially characterized in that it contains at least one compound corresponding to the formula:

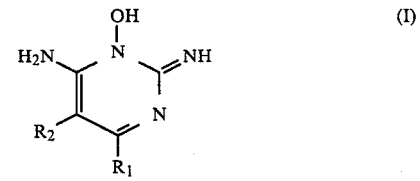

in which $R_1$ denotes a group

in which $R_3$ and $R_4$ may be chosen from amongst hydrogen, a lower alkyl, preferably containing 1 to 4 carbon atoms, alkenyl, alkylaryl or cycloalkyl group, $R_3$ and $R_4$ may also form a heterocycle with the nitrogen atom to which they are attached, chosen, inter alia, from amongst aziridinyl, azetidinyl, pyrrolidinyl, piperidyl, hexahydroazepinyl, heptamethyleneimine, octamethyleneimine, morpholine and 4-(lower alkyl)piperazinyl groups, it being possible for the heterocyclic groups to be substituted, on the carbon atoms, with one to three lower alkyl, hydroxy or alkoxy groups; the group $R_2$ is chosen from amongst hydrogen, a lower alkyl, alkenyl, alkylalkoxy, cycloalkyl, aryl, alkylaryl, arylalkyl, alkylarylalkyl, alkoxyarylalkyl and haloarylalkyl group, or cosmetically acceptable addition salts with acids, dissolved in an aqueous medium containing at least one $C_1$-$C_4$ lower alcohol and a gelling agent chosen from amongst heterobiopolysaccharides and cellulose derivatives.

In formula (I), the alkyl or alkoxy groups preferably contain from 1 to 4 carbon atoms, the alkenyl groups preferably contain from 2 to 5 carbon atoms and the aryl groups are preferably phenyl.

The more particularly preferred compounds of formula (I) are chosen from amongst compounds in which $R_2$ denotes hydrogen and $R_1$ represents a group

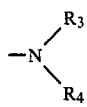

in which $R_3$ and $R_4$ form a piperidinyl ring.

The particularly preferred compound consists of 6-amino-1,2-dihydro-1-hydroxy-2-imino-4-piperidinopyrimidine which is also called "Minoxidil".

The more particularly preferred lower alcohol is ethyl alcohol.

The heterobiopolysaccharides which can be used according to the invention are synthesized by the fermentation of sugars by microorganisms. These heterobiopolysaccharides contain, in particular, mannose, glucose and glucuronic or galacturonic acid units in their chains.

More particularly, they comprise xanthan gums produced by the bacterium *Xanthomonas campestri* and the mutants or variants of the latter. Xanthan gums have a viscosity of between 0.6 and 1.65 Pa.s for an aqueous composition containing 1% xanthan gum (determined with an LVT type Brookfield viscometer, at 60 r.p.m.) and have a molecular weight of between 1,000,000 and 50,000,000.

Xanthan gums contain, in their structure, three different monosaccharides, viz. mannose, glucose and glucuronic acid in the form of a salt.

Among these products, there may be mentioned, more particularly, those marketed under the name "KELTROL T" or "TF" by KELCO, a 1% aqueous solution of which has a Brookfield LVT viscosity, at 60 r.p.m., of 1.2 to 1.6 Pa.s; "KELZAN S" marketed by KELCO, a 1% aqueous solution which has a Brookfield LVT viscosity, at 60 r.p.m., of 0.85 Pa.s; "RHODOPOL 23" and "23 SC" marketed by RHONE-POULENC, a 0.3% aqueous solution of which has a Brookfield LVT viscosity, at 30 r.p.m., of 0.45±0.05 Pa.s; "RHODIGEL 23" sold by RHONE-POULENC; "DEUTEROn XG" marketed by SCHONER GmbH, a 1% aqueous solution of which has a viscosity of 1.2 Pa.s as determined with a Brookfield LVT viscometer at 30 r.p.m; "ACTIGUM CX9, CS11 and C56", marketed by CECA/SATIA, the viscosity of a 1% aqueous solution of which is 1.2 Pa.s as determined with a Brookfield LVT viscometer at 30 r.p.m.; "KELZAN K9 C57", the viscosity of a 1% aqueous solution of which is 0.63 to 1 Pa.s as determined with a Brookfield LVS viscometer at 60 r.p.m, marketed by KELCO; "KELZAN K8 B12" the viscosity of which, as determined with a Rotovisco RVI, MVI viscometer made by HAACKE, at 25° C. is 1 Pa.s at 10 $s^{-1}$, marketed by KELCO; and "KELZAN K3 B130", also marketed by KELCO.

The heterobiopolysaccharides may also be chosen from amongst:

(a) the biopolymer "PS 87" produced by the bacterium *Bacillus polymyxa* which contains, in its structure, glucose, galactose, mannose, fucose and glucuronic acid; this polymer being described in the application EP-A-23,397;

(b) the biopolymer "S 88" produced by the strain Pseudomonas ATCC 31554, which contains, in its structure, rhamnose, glucose, mannose and glucuronic acid; this biopolymer is described in the patent UK-A-2,058,106;

(c) the biopolymer "S 130" produced by the strain Alcaligenes ATCC 31555, which contains, in its molecule, rhamnose, glucose, mannose and glucuronic acid; this biopolymer is described in the patent UK-A-2,058,107;

(d) the biopolymer "S 39" produced by the strain Pseudomonas ATCC 31644, which contains, in its molecule, rhamnose, glucose, mannose, galactose and galacturonic acid; this biopolymer is described in the patent U.S. Pat. No. 4,454,316;

(e) the biopolymer "S 198" produced by the strain Alcaligenes ATCC 31853, which contains, in its molecule, rhamnose, glucose, mannose and glucuronic acid; this biopolymer is described in the patent application EP-A-64,354; and (f) the extracellular biopolymer produced by species of gram-negative or gram-positive bacteria, yeasts, fungi or algae; this biopolymer is described in the patent application DE-A-3,224,547.

The cellulose derivatives which can be used according to the invention are represented more particularly by hydroxymethylcellulose, carboxymethylcellulose and hydroxybutylcellulose, and more particularly hydroxyethylcellulose such as the products sold under the name "CELLOSIZE" (QP and WP) by UNION CARBIDE, those sold under the name "NATROSOL" (150, 250) by HERCULES; hydroxypropylcellulose such as the products sold under the name "KLUCEL" (H, HF, HP, M, EF and G) by HERCULES; methylhydroxyethylcellulose such as the product sold under the name "TYLOSE MH 300" by HOECHST and methylhydroxypropylcellulose such as the product sold under the name "METHOCEL" (E, F, J and K) by DOW CHEMICAL.

In the compositions according to the invention, the piperidinopyrimidine derivative is preferably employed in proportions of between 0.1 and 5% by weight and preferably between 0.1 and 2% by weight relative to the total weight of the composition.

The aqueous medium which enables the piperidinopyrimidine to be solubilized preferably comprises from 40 to 80% by weight of water, in particular from 40 to 60%, and from 15 to 60% by weight of a lower alcohol such as, for example, isopropyl or tert-butyl alcohols, and in particular ethyl alcohol, in proportions preferably between 15 and 40% by weight, these proportions being given relative to the total weight of the composition.

The gelling agent is preferably employed in proportions from 0.5 to 5% and in particular from 1 to 3% by weight relative to the total weight of the gelled cosmetic composition.

In the case where a heteropolysaccharide such as xanthan gum is employed, the concentration is preferably less than 1% by weight.

The gelled medium may optionally contain other solvents in proportions by weight not exceeding 20% by weight relative to the aqueous medium and more particularly, it may contain solvents chosen from amongst alkylene glycol or dialkylene glycol alkyl ethers which include the products marketed under the name "DOWANOL PM, EE and DE", sold by DOW CHEMICAL, straight-chained or branched $C_1$-$C_6$ alcohols other than the lower alcohol defined above or propylene glycol.

These compositions may take various forms and may be packaged, inter alia, in tubes and dispensed easily in the form of strips which can be squeezed out and which can be well localized at the point of application. They generally have a pleasant, colourless and translucent appearance.

The treatment method for the control of loss of hair and for inducing or stimulating the growth of the latter, mainly consists in applying to the alopecic regions of the scalp and the hair of an individual, a composition according to the invention, for example after washing the scalp and the hair with a shampoo or shortly after shampooing.

The Applicant Company has observed a significant increase in the ratio $$\frac{A}{T} \quad \frac{\text{(number of hairs in the anagen phase)}}{\text{(number of hairs in the telogen phase)}}$$

as early as during the first month of treatment, and an extension of the anagen phase, which is particularly surprising, in particular for xanthan gums or cellulose derivatives, considering their low Minoxidil-releasing properties described in the prior art.

This method particularly has the features of a cosmetic method insofar as it enables the hair or the scalp to be looked after in the cosmetic sense of the term, i.e. to supply them with substances they lack and to beautify them.

Moreover, it has the features of a pharmaceutical treatment method insofar as the active substance has a therapeutic activity with regard to the biological mechanisms of the pilar cycle.

The following examples are intended to illustrate the invention without, however, being limiting in nature.

EXAMPLES

Gels effective in stimulating hair growth, with the following composition, were prepared:

| EXAMPLE No. | 1 | 2 | 3 | 4 | 5 | 6 |
|---|---|---|---|---|---|---|
| 6-Amino-1,2-dihydro-1-hydroxy-2-imino-4-piperidinopyrimidine in g AS | 0.25 | 1 | 0.5 | 1 | 0.75 | 1 |
| Hydroxyethylcellulose in g AS | | | | | | |
| Cellosize QP | 1 | | | | | |
| Cellosize WP | | 5 | | | | |
| Natrosol 250 | | | 1 | | | |
| Hydroxypropylcellulose in g AS Klucel EF | | | | | | 5 |
| Methylhydroxyethyl-cellulose in g AS Tylose MH 300 | | | | 2 | | |
| Methylhydroxypropyl-cellulose in g AS Methocel F | | | | | 1 | |
| Ethyl alcohol in g | 16.2 | 40.5 | 32.4 | 40.5 | 36.5 | 40.5 |
| Water qs g | 100 | 100 | 100 | 100 | 100 | 100 |
| Epprecht-drage viscosity in Pa.s at 25° C. | | | | | | |
| module 2 | 0.225 | 0.42 | | 0.39 | 0.19 | 0.09 |
| module 3 | | | 0.79 | | | |

| EXAMPLE No. | 7 | 8 | 9 | 10 | 11 | 12 |
|---|---|---|---|---|---|---|
| 6-Amino-1,2-dihydro-1-hydroxy-2-imino-4-piperidinopyrimidine in g AS | 1 | 2.5 | 3 | 4 | 1 | 1.5 |
| Hydroxypropylcellulose in g AS Klucel G | 3 | | | | | |
| Heteropolysaccharides n g AS | | | | | | |
| Rhodopol SC | | 0.75 | | | | |
| Kelzan K8 B12 | | | 1 | | | |
| Kelzan K9 C57 | | | | 1 | | |
| Actigum CS11 | | | | | 0.75 | |
| Actigum C56 | | | | | | 1 |
| Ethyl alcohol in g | 48.6 | 24.3 | 40.5 | 40.5 | 28.4 | 28.4 |
| Propylene glycol monomethyl ether sold under the name DOWANOL PM by DOW CHEMICAL in g AS | | 15 | 20 | 20 | | 10 |
| Water qs g | 100 | 100 | 100 | 100 | 100 | 100 |
| Epprecht-Drage viscosity in Pa.s at 25° C. | | | | | | |
| at 25° C. module 2 | | 0.14 | | | 0.04 | 0.03 |
| module 3 | 0.55 | | 1.74 | 1.15 | | |

| EXAMPLE No. | 13 | 14 |
|---|---|---|
| 6-Amino-1,2-dihydro-1-hydroxy-2-imino-4-piperidinopyrimidine in g AS | 3 | 3 |
| Heteropolysaccharide in g AS Keltrol T | 1 | |
| Hydroxypropylcellulose in g AS Klucel G | | 3 |
| Isopropyl alcohol in g | 39.5 | |
| tert-Butyl alcohol in g | | 39.5 |
| Water qs g | 100 | 100 |
| Epprecht-Drage viscosity in Pa.s at 25° C. module 3 | 0.23 | 0.72 |

EXAMPLE 15

The following composition is prepared:

| Minoxidil | 2 g |
|---|---|
| Keltrol T | 0.75 g |
| Dowanol PM | 20 g |
| Ethyl alcohol | 40.5 g |
| Water qs | 100 g |

APPLICATION EXAMPLE 1

Between 1 and 2 g of the composition according to the invention with a "Minoxidil" content of 3% by weight are applied to the alopecic region (the area of which is 200 to 300 cm²) of the scalp of four women, at a frequency of one application per day, five days per week; the efficacy of the treatment is monitored once a month with a phototrichogram.

It is observed that, in comparison with an alopecic region treated with a lotion of conventional composition, i.e. containing 5% by weight of "Minoxidil" in a propylene glycol-ethyl alcohol-water mixture, and applied more frequently (two applications per day, five days per week), the activity of the composition according to the invention with regard to improvement in the condition of the hair appears in the form of an increase in the total hair density (increase in the sum: anagens+telogens/cm$^2$).

This composition is as effective, right from the first month of treatment, as the conventional lotion applied more frequently and containing a larger amount of "Minoxidil".

APPLICATION EXAMPLE 2

Applying the composition in Example 15 as mentioned in application example 1, an increase of nearly 60% in the A/T ratio is observed after 3 months, the increase in this ratio being of the order of 15% in the case of the compositions which do not contain xanthan gum.

I claim:

1. Composition in the form of a gel for inducing and stimulating hair growth and for decreasing hair loss, said composition comprising an effective amount of at least one compound of formula (I):

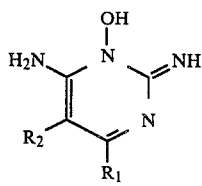

wherein $R_1$ denotes a group

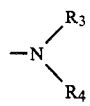

wherein $R_3$ and $R_4$ are selected from the group consisting of hydrogen, lower alkyl, preferably containing 1 to 4 carbon atoms, alkenyl, alkylaryl and cycloalkyl, or $R_3$ and $R_4$ together form a heterocycle with the nitrogen atom to which they are attached selected from the group consisting of aziridinyl, azetidinyl, pyrrolidinyl, piperidino, hexahydroazepinyl, heptamethyleneimino, octamethyleneimino, morpholino and 4-(lower alkyl)-piperazinyl, the heterocyclic groups being unsubstituted or substituted on the carbon atoms with one to three lower alkyl, hydroxy or alkoxy; and wherein $R_2$ is selected from the group consisting of hydrogen, lower alkyl, alkenyl, alkylalkoxy, cycloalkyl, aryl, alkylaryl, arylalkyl, alkylarylalkyl, alkoxyarylalkyl and haloarylalkyl group, or cosmetically acceptable addition salts with acids, dissolved in an aqueous medium comprising at least one C$_1$-C$_4$ lower alcohol and a gelling agent selected from the group consisting of heterobiopolysaccharides synthesized by fermentation of sugars by microorganisms and cellulose derivatives.

2. Composition according to claim 1, wherein the compound of formula (I) is 6-amino-1,2-dihydro-1-hydroxy-2-imino-4-piperidinopyrimidine.

3. Composition according to claim 1, wherein the lower alcohol is ethyl alcohol, isopropyl alcohol or tert-butyl alcohol.

4. Composition according to any one of claims 1, wherein the heterobiopolysaccharide contains mannose, glucose and glucuronic or galacturonic acid units in its chain.

5. Composition according to claim 1, wherein the heterobiopolysaccharide is xanthan gum with a molecular weight from 1,000,000 to 50,000,000.

6. Composition according to claim 1, wherein the cellulose derivative is selected from the group consisting of hydroxymethylcellulose, carboxymethylcellulose, hydroxybutylcellulose, hydroxyethylcellulose, hydroxypropylcellulose, methylhydroxyethylcellulose and methylhydroxypropylcellulose.

7. Composition according to claim 1, wherein the compound of formula (I) is present in proportions from 0.1 to 5% by weight relative to the total weight of the composition.

8. Composition according to claim 1, wherein the aqueous medium comprises 40 to 80% by weight of water and 15 to 60% by weight of a lower alcohol, relative to the total weight of the composition.

9. Composition according to claim 1, containing 0.5 to 5% of gelling agent.

10. Composition according to claim 9, containing a heterobiopolysaccharide in proportions of less than 1% by weight relative to the total weight of the composition.

11. Composition according to claim 1, containing solvents in addition to the aqueous medium containing at least one C$_1$-C$_4$ lower alcohol in proportions not exceeding 20% by weight relative to the aqueous medium.

12. Composition according to claim 11, wherein the solvent is alkylene glycol or dialkylene glycol alkyl ethers or straight-chain or branched C$_1$-C$_6$ alcohols other than the C$_1$-C$_4$ lower alcohol defined in claim 1 or propylene glycol.

13. Method for cosmetic treatment of hair, comprising the composition as defined in claim 1 to the scalp or the hair.

14. Process for inducing and stimulating hair growth or decreasing their loss, comprising applying on the scalp or the hair the composition as defined in claim 1.

* * * * *